US012357730B2

(12) United States Patent
Morris

(10) Patent No.: US 12,357,730 B2
(45) Date of Patent: Jul. 15, 2025

(54) FIBER-REINFORCED BIO-MATERIAL COMPOSITION AND METHODS OF USE

(71) Applicant: Bone Solutions, Inc., Colleyville, TX (US)

(72) Inventor: Frankie L. Morris, Colleyville, TX (US)

(73) Assignee: Bone Solutions, Inc., Colleyville, TX (US)

( * ) Notice: Subject to any disclaimer, the term of this patent is extended or adjusted under 35 U.S.C. 154(b) by 0 days.

(21) Appl. No.: 17/969,309

(22) Filed: Oct. 19, 2022

(65) Prior Publication Data

US 2023/0121071 A1   Apr. 20, 2023

Related U.S. Application Data

(60) Provisional application No. 63/257,643, filed on Oct. 20, 2021.

(51) Int. Cl.
*A61L 27/48* (2006.01)
*A61L 27/54* (2006.01)
(Continued)

(52) U.S. Cl.
CPC ............ *A61L 27/48* (2013.01); *A61L 27/54* (2013.01); *A61L 27/56* (2013.01); *A61L 27/58* (2013.01);
(Continued)

(58) Field of Classification Search
CPC ........ A61L 27/58; A61L 27/047; A61L 27/12; A61L 27/18; A61L 27/20; A61L 27/54;
(Continued)

(56) References Cited

U.S. PATENT DOCUMENTS

| 2009/0270527 A1* | 10/2009 | Lin ...................... A61L 24/046 523/116 |
| 2012/0121660 A1* | 5/2012 | Akella ................... A61L 27/46 424/549 |
| 2018/0326124 A1* | 11/2018 | Diaz ....................... A61L 27/18 |

OTHER PUBLICATIONS

Van Vugt et al., "Biomaterials in treatment of orthopedic infections." Nov. 4, 2016. Woodhead, 2017, pp. 41-68. https://doi.org/10.1016/B978-0-08-100205-6.00003-3. RetrievedDec. 12, 2023 through https://www.sciencedirect.com/topics/pharmacology-toxicology-and-pharmaceutical-science/bioactive-glass. (Year: 2017).*

(Continued)

*Primary Examiner* — Benjamin J Packard
*Assistant Examiner* — Lucy M Tien
(74) *Attorney, Agent, or Firm* — McDonnell Boehnen Hulbert & Berghoff LLP

(57) ABSTRACT

The present disclosure provides bio-material composition, comprising a dry potassium phosphate based mixture comprising: MgO, monobasic potassium phosphate, monobasic sodium phosphate, proteoglycans, calcium sodium phosphosilicate, and a plurality of spherically-shaped polymers, wherein a weight percent ratio of monobasic potassium phosphate to MgO is between about 3:1 and 1:1, wherein the dry potassium phosphate based mixture is configured to be mixed with the aqueous solution to thereby form a reabsorbable bio-material slurry, wherein the spherically-shaped polymers are between about 1-5 weight percent of the dry composition, and wherein the spherically-shaped polymers are absorbed faster than the remaining components of the reabsorbable bio-material slurry to thereby form pockets within the bio-material composition that enhance reabsorption of the bio-material composition.

25 Claims, 1 Drawing Sheet

(51) Int. Cl.
    *A61L 27/56* (2006.01)
    *A61L 27/58* (2006.01)
(52) U.S. Cl.
    CPC ... *A61L 2300/252* (2013.01); *A61L 2300/406* (2013.01); *A61L 2430/02* (2013.01)
(58) Field of Classification Search
    CPC .............. A61L 27/56; A61L 2300/406; A61L 2430/02; A61L 27/48; A61L 2300/252; A61L 27/46
    See application file for complete search history.

(56) References Cited

OTHER PUBLICATIONS

Lin, Zhiyun, et al. "Precisely Controlled Delivery of Magnesium Ions Thru Sponge-like Monodisperse PLGA/nano-MgO-alginate Core-shell Microsphere Device to Enable In-situ Bone Regeneration." Biomaterials, vol. 174, Aug. 2018, pp. 1-16. https://doi.org/10.1016/j.biomaterials.2018.05.011. (Year: 2018).*

"Alginate Gel." Phycological Society of America, https://web.archive.org/web/20150905113609/www.psaalgae.org/alginate-gel (Year: 2015).*

\* cited by examiner

FIBER-REINFORCED BIO-MATERIAL COMPOSITION AND METHODS OF USE

RELATED APPLICATIONS

This application claims priority to U.S. Provisional Application No. 63/257,643 entitled "Fiber-Reinforced Bio-Material Composition and Methods of Use," filed on Oct. 20, 2021, the contents of which are hereby incorporated by reference in its entirety.

TECHNICAL FIELD

The present disclosure relates to a method for treating bone defects, particularly to prevent cortical bone deterioration.

BACKGROUND

Unless otherwise indicated herein, the materials described in this section are not admitted to be prior art to the claims in this application.

Bone defects by definition are a lack of bone tissue in a body area, where bone should normally be. Such bone defects can cause pain and limit mobility. As non-limiting examples, such bone defects may include a bone cyst, a bone marrow lesion, an osteoporotic bone, an osteochondral defect, an insufficiency fracture, and osteoarthristis. The bone defects of the listed above may be defects of the extremities and/or pelvic bone, as specific examples.

What is needed in the art is a method for treating bone defects that supplies a high compressive strength material with fast absorption so that the bone void filler material breaks down faster in the bone defect area and rapidly turns into bone to provide improved strength.

SUMMARY

In view of the foregoing, the present disclosure comprises a bio-material composition and method of producing such, wherein one or more of the embodiments formed are osteoconductive and osteoinductive, thereby enabling new bone growth in the patient in bone defect areas.

In a first aspect, the present disclosure provides bio-material composition, comprising a dry potassium phosphate based mixture comprising: MgO, monobasic potassium phosphate, monobasic sodium phosphate, proteoglycans, calcium sodium phosphosilicate, and a plurality of spherically-shaped polymers, wherein a weight percent ratio of monobasic potassium phosphate to MgO is between about 3:1 and 1:1, wherein the dry potassium phosphate based mixture is configured to be mixed with the aqueous solution to thereby form a reabsorbable bio-material slurry, wherein the spherically-shaped polymers are between about 1-5 weight percent of the dry composition, and wherein the spherically-shaped polymers are absorbed faster than the remaining components of the reabsorbable bio-material slurry to thereby form pockets within the bio-material composition that enhance reabsorption of the bio-material composition.

In a second aspect, the present disclosure provides a method for treating a bone defect using a bio-material with increased porosity and reabsorption characteristics, the method comprising: (a) mixing a dry potassium phosphate based mixture with an aqueous solution to form a reabsorbable bio-material slurry, wherein the dry potassium phosphate based mixture comprises MgO, monobasic potassium phosphate, monobasic sodium phosphate, proteoglycans, calcium sodium phosphosilicate, and a plurality of spherically-shaped polymers, wherein a weight percent ratio of monobasic potassium phosphate to MgO is between about 3:1 and 1:1, wherein the dry potassium phosphate based mixture is configured to be mixed with the aqueous solution to thereby form a reabsorbable bio-material slurry, wherein the spherically-shaped polymers are between about 1-5 weight percent of the dry composition, and wherein the spherically-shaped polymers are absorbed faster than the remaining components of the reabsorbable bio-material slurry to thereby form pockets within the bio-material composition that enhance reabsorption of the bio-material composition, (b) accessing a void of a bone defect within a bone, and (c) filling the void with the reabsorbable bio-material slurry, wherein the reabsorbable bio-material slurry is osteoconductive and osteoinductive, thereby enabling new bone growth in the void.

These as well as other aspects, advantages, and alternatives, will become apparent to those of ordinary skill in the art by reading the following detailed description, with reference where appropriate to the accompanying drawings.

DETAILED DESCRIPTION

Figure 1C:
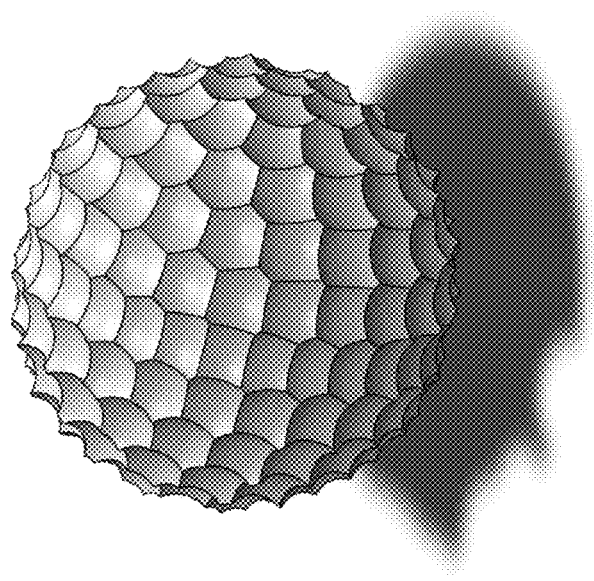
FIGS. 1A-1C illustrate various spherically-shaped reabsorbable polymers, according to exemplary embodiments.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The exemplary embodiments described herein are not meant to be limiting. It will be readily understood that the aspects of the present disclosure, as generally described herein and illustrated in the FIGURES, can be arranged, substituted, combined, separated, and designed in a wide variety of different configurations, all of which are explicitly contemplated herein.

Furthermore, the particular arrangements shown in the FIGURES should not be viewed as limiting. It should be understood that other embodiments may include more or less of each element shown in a given FIGURE. Further, some of the illustrated elements may be combined or omitted. Yet further, an exemplary embodiment may include elements that are not illustrated in the FIGURES.

As used herein, with respect to measurements, "about" means +/−5%.

As used herein, "osteostimulative" refers to the ability of a material to improve healing of bone injuries or defects.

As used herein, "osteoconductive" refers to the ability of a material to serve as a scaffold for viable bone growth and healing.

As used herein, "osteoinductive" refers to the capacity of a material to stimulate or induce bone growth.

As used herein, "biocompatible" refers to a material that elicits no significant undesirable response when inserted into a recipient (e.g., a mammalian, including human, recipient).

As used herein, "reabsorbable" refers to a materials ability to be absorbed in-vivo through bodily processes. The absorbed material may turn into bone in the patient's body.

The present disclosure provides a bio-material composition comprising a dry potassium phosphate based mixture comprising: MgO, monobasic potassium phosphate, monobasic sodium phosphate, proteoglycans, calcium sodium phosphosilicate, and a plurality of spherically-shaped polymers. A weight percent ratio of monobasic potassium phosphate to MgO is between about 3:1 and 1:1. The dry potassium phosphate based mixture is configured to be mixed with the aqueous solution to thereby form a reabsorbable bio-material slurry, as discussed in additional detail below. The spherically-shaped polymers are between about 1-5 weight percent of the dry composition. The spherically-shaped polymers are absorbed faster than the remaining components of the reabsorbable bio-material slurry to thereby form pockets within the bio-material composition that enhance reabsorption of the bio-material composition.

Among various examples, the spherically-shaped polymers may be between about 1.5-2.5 weight percent of the dry composition, between about 1.5-3 weight percent of the dry composition, between about 1.5-3.5 weight percent of the dry composition, between about 1.5-4 weight percent of the dry composition, between about 1.5-4.5 weight percent of the dry composition, about 2 weight percent of the dry composition, between about 1.5-2 weight percent of the dry composition, or between about 1.5-2.5 weight percent of the dry composition.

Figure 1B:
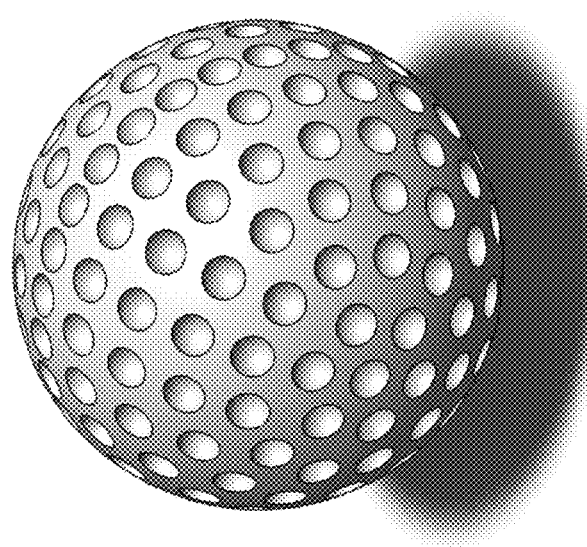
Figure 1A:
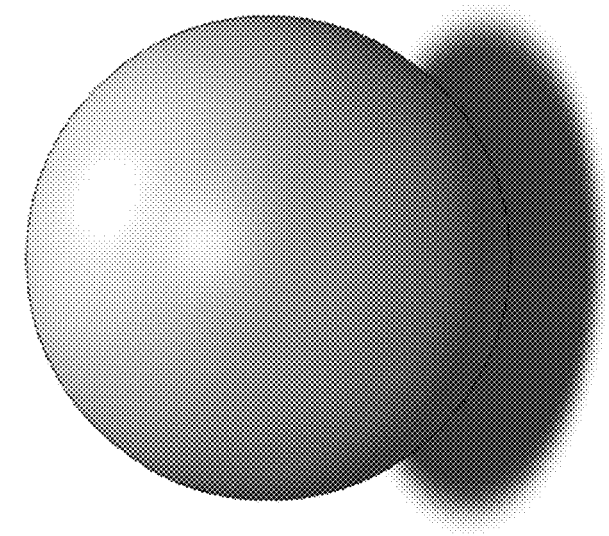

The spherically-shaped polymers may take a variety of forms. In one example, the spherically-shaped polymers comprise a powder. In another example, as shown in FIG. 1A, the spherically-shaped polymers comprise smooth spheres. In another example, as shown in FIG. 1B, the spherically-shaped polymers comprise spheres with a plurality of indentations. In another example, as shown in FIG. 1C, the spherically-shaped polymers comprise spheres with a plurality of protrusions.

In one example, the spherically-shaped polymers comprise poly(lactic-co-glycolic acid) (PLGA). In another example, the spherically-shaped polymers comprise poly(glycolic acid) (PGA). Other materials are possible as well.

In various examples, the bio-material composition comprises mono potassium phosphate between about 44-61% of the total composition. The mono potassium phosphate provides faster absorption of the composition. The bio-material composition also comprises calcium sodium phosphosilicate between about 4-9% of the total composition. The calcium sodium phosphosilicate provides additional strength and platform for bone growth and helps provide improved handling characteristics. The bio-material composition also comprises mono sodium phosphate between about 4-9% of the total composition, which helps control ion release. The bio-material composition also comprises magnesium oxide between about 30-45% of the total composition, which may be hard burned to provide controlled reactivity. The MgO enables the composition to be reabsorbed faster compared to existing calcium bone void fillers. The MgO stimulates osteoblast activity as osteoblasts use magnesium as fuel in the bone formation process. The bio-material composition also comprises proteoglycans between about 0-5% of the total composition. The proteoglycans are osteoconductive and osteoinductive because it allows for new bone growth along the bone-implant interface as well as within the bone-implant interface. The bio-material composition also comprises phosphoric acid between about 0-5% of the total composition, which helps break down MgO to generate more phosphate. Various combinations of the above components and percentages are possible as well.

The bio-material composition may be applied to various sites including but not limited to sites on or adjacent to bone; sites on, in, or adjacent to a cartilage; sites in, on, or proximate to bone or cartilage, and bone or cartilage contacting surfaces of implant devices. The bio-material composition may be applied directly to bone defects acting as a bone filler, bone cement, delivery device, bone graft and/or general binder matrix. Alternatively, the bio-material composition may be used in conjunction with various fixation devices such as anchors including screws and plates.

Water (or another aqueous solution) can be added in a large range of weight percents generally ranging from about 15-40 weight percent, preferably between about 20-35 weight percent and even more preferably between about 28-32 weight percent. It was found that a saline solution may be used. An exemplary saline solution is a 0.9% saline solution. As another example, the aqueous solution comprises blood (e.g., the blood from the patient or blood other than that of the patient). In yet another example, the aqueous solution comprises sodium chloride (about 0.75 weight percent), monosodium phosphate ($NaH_2PO_4$) (about 16.60 weight percent), and water (about 82.65 weight percent). Other aqueous solutions are possible as well.

The dry mixture is preferably activated on-site. Activation comprises mixing the dry composition with an aqueous solution (such as in a sterile mixing vessel to form a reabsorbable bio-material slurry). Water (e.g., sterile water (or other sterile aqueous solution, e.g., i.e., slight saline solution) is generally added up to about 40% of the dry weight, although the amount of water can be adjusted to form a bio-material of varying viscosity. In one embodiment, the mixing vessel and any utensils are sterilized prior to use. Various mixing vessels can be used including but not limited to a sterile medicine cup, bowl, dish, basin or other sterile container. In another example, the aqueous solution comprises blood (e.g., the blood from the patient or blood other than that of the patient).

The dry components of the mixture can be mixed using a variety of methods including hand mixing or machine mixing. One method for mixing, sizing, and homogenizing the various powders is via vibratory milling. Another homogenization method utilizes a ribbon mixer wherein the particles are ground to a fine size. It may be preferable to mix the dry components again on-site before the addition of the activating aqueous solution. One preferred method is to hand mix with a sterile spatula or other mixture utensil. The reabsorbable bio-material slurry is typically hand mixed for between about 1-10 minutes, although mixing times can be adjusted depending upon conditions and mixing means.

The reabsorbable bio-material slurry can be created in injectable, paste, puddy and other forms. Because the slurry is produced at the user site, the consistency of the material can be manipulated by varying the amount of water added to the dry mixture. Increasing the water content generally increases the flowability while decreasing the water content tends to thicken the slurry.

Working times can be increased or decreased by varying the temperatures of bio-material components. Higher temperature components tend to react and set quicker than cooler components. Thus regulating the temperature of the water (or other reactants) can be an effective way to regulate working time.

In one example, a phosphoric acid solution may be used instead of water. Such an embodiment increases the bonding strength of the material. The molarity of the phosphoric acid can vary, as long as the eventual pH of the slurry is not hazardous to the patient, or contraindicative to healing.

Once the reabsorbable bio-material slurry has been formed it is applied to (and optionally also around) the site of desired cartilage growth. The slurry can be applied to the site in a number of ways including but not limited to spreading an amount of the material to the site using a sterile spatula, tongue blade, knife or other sterile implement useful for spreading a paste or puddy-like material. In some situations it may be preferable to use a relatively thick consistency like a paste or puddy when applying the activated slurry, since such consistencies tend to stick to bone and other surface more easily than thinner ones. If an injectable formation is desired, it can be applied using a syringe or other similar device.

Various antibiotics or other antibacterial and anti-viral compositions and agents can be added to the composition between about 1-5 percent of the dry composition. The invented bio-material can act as a delivery device or the antibiotics can be added to protect against bacterial infection during surgery.

Cationic antibiotics, especially aminoglycosides and certain peptide antibiotics may be most desirable when incorporating drugs into the bio-material. Suitable aminoglycosides include but are not limited to: amikacin, butirosin, dideoxykanamycin, fortimycin, gentamycin, kanamycin, lividomycin, neomycin, netilmicin, ribostamycin, sagamycin, seldomycin and epimers thereof, sisomycin, sorbistin, spectinomycin and tobramycin. Using inorganic salts like sulfates, phosphates, hydrogenphosphates may be preferable, sulfates being the most preferable. Growth factors include but are not limited to growth factors like transforming growth factor TGF-β. Vancomycin and similar antibiotics can also be used.

In another example, the present disclosure provides a method for treating a bone defect using a bio-material with increased porosity and reabsorption characteristics. The method includes (a) mixing a dry potassium phosphate based mixture with an aqueous solution to form a reabsorbable bio-material slurry, wherein the dry potassium phosphate based mixture comprises MgO, monobasic potassium phosphate, monobasic sodium phosphate, proteoglycans, calcium sodium phosphosilicate, and a plurality of spherically-shaped polymers, wherein a weight percent ratio of monobasic potassium phosphate to MgO is between about 3:1 and 1:1, wherein the dry potassium phosphate based mixture is configured to be mixed with the aqueous solution to thereby form a reabsorbable bio-material slurry, wherein the spherically-shaped polymers are between about 1-5 weight percent of the dry composition, and wherein the spherically-shaped polymers are absorbed faster than the remaining components of the reabsorbable bio-material slurry to thereby form pockets within the bio-material composition that enhance reabsorption of the bio-material composition, (b) accessing a void of a bone defect within a bone, and (c) filling the void with the reabsorbable bio-material slurry, wherein the reabsorbable bio-material slurry is osteoconductive and osteoinductive, thereby enabling new bone growth in the void. The proteoglycans act as active regulators of collagen fibrillogenesis to thereby structure tissue of a patient by organizing a bone extracellular matrix.

In such a method, the reabsorbable bio-material slurry turns to bone to provide improved bone structure in the bone. In contrast, traditional calcium-based bone fillers provide a scaffolding on which bone can grow, but do not turn into bone like the above-described composition. As such, the osteocytes in traditional calcium-based bone fillers run out and the bone filler deteriorates and is reabsorbed into the body. The advantage of the reabsorbable bio-material slurry described herein is that it actually turns into bone to thereby provide improved bone structure. In addition, the reabsorbable bio-material slurry described herein increases osteoblast activity in the bone due to the magnesium present in the reabsorbable bio-material slurry. Osteoblasts are the major cellular component of bone. Osteoblasts are specialized, terminally differentiated products of mesenchymal stem cells. They synthesize dense, crosslinked collagen and specialized proteins in much smaller quantities, including osteocalcin and osteopontin, which compose the organic matrix of bone. As such, the above method comprises a method for preserving bone comprising stimulating osteoblasts due to the magnesium present in the reabsorbable bio-material slurry to help maintain bone structure. The reabsorbable bio-material slurry described herein supplies a high compressive strength material with fast absorption so that the reabsorbable bio-material slurry breaks down faster in the bone defect area and rapidly turns into bone to provide improved strength in the bone.

As discussed above, the method includes accessing a void of a bone defect within a bone. The bone defect may take a variety of forms. In particular, the bone defect may be selected from a group consisting of: a bone cyst, a bone marrow lesion, an osteoporotic bone, an osteochondral defect, an insufficiency fracture, and osteoarthristis. A bone cyst is a fluid-filled hole that develops inside a bone. They mostly occur in children and young adults. Bone cysts do not usually cause any symptoms, they are not cancerous and they do not usually pose a serious threat to health. Bone marrow lesions (BMLs) or using older terminology "bone marrow edema" is characterized by excessive water signals in the marrow space on magnetic resonance imaging or ultrasound; BMLs constitute a central component of a wide variety of inflammatory and non-inflammatory rheumatologic conditions affecting the musculoskeletal system: BMLs are not only considered significant sources of pain but also linked to increased disease activity in many musculoskeletal conditions (for example, osteoarthritis, rheumatoid arthritis). An osteoporotic bone is an indication of osteoporosis, which is a bone disease that occurs when the body loses too much bone, makes too little bone, or both. As a result, bones become weak and may break from a fall or, in serious cases, from sneezing or minor bumps. An osteochondral defect refers to a focal area of damage that involves both the cartilage and a piece of underlying bone. These can occur from an acute traumatic injury to the knee or an underlying disorder of the bone. An insufficiency fracture (or stress fracture) is a crack in a bone that occurs without a definite injury. It occurs as result of repetitive activity as opposed to a single traumatic event that causes a more traditional break or fracture. They are much more common in the lower extremity as these bones are considered weight-bearing. Osteoarthritis is the most common form of arthritis, affecting the hands, knees, hips, spine and other joints. Characteristics of osteoarthritis include a loss of cartilage, seen as a reduction in the joint space, and osteophytes (or bone spurs).

In one example, the method further includes positioning an anchor adjacent the void prior to filling the void with the reabsorbable bio-material slurry. Such an anchor provides additional structural support for the bone. The anchor may comprise a plate and screws, as a non-limiting example. In one example, the anchor the anchor comprises a polymer or a metal. In another example, the anchor comprises a reabsorbable material such that the entirety of the anchor turns to bone over time. In one such example, the anchor comprises the reabsorbable bio-material slurry material.

In another example, the method further comprises removing at least a portion of the bone defect prior to filling the void with the reabsorbable bio-material slurry. In one such example, the portion of the bone defect may be removed by a reamer prior to filling the void with the reabsorbable bio-material slurry.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Because many modifications, variations, and changes in detail can be made to the described example, it is intended that all matters in the preceding description and shown in the accompanying FIGURES be interpreted as illustrative and not in a limiting sense. Further, it is intended to be understood that the following clauses (and any combination of the clauses) further describe aspects of the present description.

What is claimed is:

1. A bio-material composition, comprising:
   a dry potassium phosphate based mixture comprising: MgO present in an amount in between 30-45% of the total composition, monobasic potassium phosphate present in an amount in the range of 44-61% of the total composition, monobasic sodium phosphate present in an amount in the range of 4-9% of the total composition, proteoglycans present in an amount between 1-5% of the total composition, calcium sodium phosphosilicate present in an amount between 4-9% of the total composition, and a plurality of spherically-shaped polymers consisting of poly(lactic-co-glycolic acid) (PLGA) or poly(glycolic acid) (PGA), wherein a weight percent ratio of monobasic potassium phosphate to MgO is between about 3:1 and 1:1, wherein the dry potassium phosphate based mixture is mixed with an aqueous solution to form a reabsorbable bio-material slurry, wherein the plurality of spherically-shaped polymers are between about 1-5 weight percent of the dry potassium phosphate based mixture, and wherein the plurality of spherically-shaped polymers are absorbed faster than the remaining components of the reabsorbable bio-material slurry to thereby form pockets within the bio-material composition that enhance reabsorption of the bio-material composition.

2. The bio-material composition of claim 1, wherein the proteoglycans are selected from the group consisting of: mineral-collagen composite matrix, fibers, granules, morcellized fibers, nanoparticles, and combinations thereof.

3. The bio-material composition of claim 1, wherein the calcium sodium phosphosilicate is selected from a group consisting of: bioactive glass fibers, silica bioactive glass, Silicate, and combinations thereof.

4. The bio-material composition of claim 1, wherein the plurality of spherically-shaped polymers are between about 1.5-2.5 weight percent of the dry potassium phosphate based mixture.

5. The bio-material composition of claim 1, wherein the plurality of spherically-shaped polymers are between about 1.5-3 weight percent of the dry potassium phosphate based mixture.

6. The bio-material composition of claim 1, wherein the plurality of spherically-shaped polymers are between about 1.5-3.5 weight percent of the dry potassium phosphate based mixture.

7. The bio-material composition of claim 1, wherein the plurality of spherically-shaped polymers are between about 1.5-4 weight percent of the dry potassium phosphate based mixture.

8. The bio-material composition of claim 1, wherein the plurality of spherically-shaped polymers are between about 1.5-4.5 weight percent of the dry potassium phosphate based mixture.

9. The bio-material composition of claim 1, wherein the plurality of spherically-shaped polymers are about 2 weight percent of the dry potassium phosphate based mixture.

10. The bio-material composition of claim 1, wherein the plurality of spherically-shaped polymers are between about 1.5-2 weight percent of the dry potassium phosphate based mixture.

11. The bio-material composition of claim 1, wherein the bio-material composition is osteoconductive and osteoinductive, thereby enabling new bone growth in a patient along a bone-implant interface as well as within the bone-implant interface.

12. The bio-material composition of claim 1, wherein the dry potassium phosphate based mixture further comprises an antibiotic between about 1-5 percent of the dry potassium phosphate based mixture.

13. The bio-material composition of claim 12, wherein the antibiotic is an aminoglycoside antibiotic.

14. The bio-material composition of claim 1, wherein the plurality of spherically-shaped polymers comprise a powder.

15. The bio-material composition of claim 1, wherein the plurality of spherically-shaped polymers comprise spheres.

16. The bio-material composition of claim 1, wherein the plurality of spherically-shaped polymers comprise spheres with a plurality of indentations.

17. The bio-material composition of claim 1, wherein the plurality of spherically-shaped polymers comprise spheres with a plurality of protrusions.

18. A method for treating a bone defect using a bio-material with increased porosity and reabsorption characteristics, the method comprising:
   mixing a dry potassium phosphate based mixture with an aqueous solution to form a reabsorbable bio-material slurry, wherein the dry potassium phosphate based mixture comprises MgO present in an amount in between 30-45% of the total composition, monobasic potassium phosphate present in an amount in the range of 44-61% of the total composition, monobasic sodium phosphate present in an amount in the range of 4-9% of the total composition, proteoglycans, calcium sodium phosphosilicate, and a plurality of spherically-shaped polymers consisting of poly(lactic-co-glycolic acid) (PLGA) or poly(glycolic acid) (PGA), wherein a weight percent ratio of monobasic potassium phosphate to MgO is between about 3:1 and 1:1, wherein the dry potassium phosphate based mixture is mixed with the aqueous solution to form the reabsorbable bio-material slurry, wherein the plurality of spherically-shaped polymers are between about 1-5 weight percent of the dry potassium phosphate based mixture, and wherein the plurality of spherically-shaped polymers are absorbed faster than the remaining components of the reabsorbable bio-material slurry to thereby form pockets within the bio-material composition that enhance reabsorption of the bio-material composition;

accessing a void of the bone defect within a bone; and filling the void with the reabsorbable bio-material slurry, wherein the reabsorbable bio-material slurry is osteo-conductive and osteoinductive, thereby enabling new bone growth in the void.

19. The method of claim 18, wherein the reabsorbable bio-material slurry turns to bone to provide bone structure in the bone.

20. The method of claim 18, wherein the bone defect is selected from a group consisting of: a bone cyst, a bone marrow lesion, an osteoporotic bone, an osteochondral defect, an insufficiency fracture, and osteoarthritis.

21. The method of claim 18, wherein the dry potassium phosphate based mixture further comprises an antibiotic.

22. The method of claim 18, further comprising:

positioning an anchor adjacent the void prior to filling the void with the reabsorbable bio-material slurry, wherein the anchor provides additional structural support for the bone.

23. The method of claim 22, wherein the anchor comprises a polymer or a metal.

24. The method of claim 22, wherein the anchor comprises a reabsorbable material.

25. The method of claim 18, further comprising:

removing at least a portion of the bone defect prior to filling the void with the reabsorbable bio-material slurry.

* * * * *